US010852307B2

(12) United States Patent
Leung et al.

(10) Patent No.: US 10,852,307 B2
(45) Date of Patent: Dec. 1, 2020

(54) METHODS OF DETECTING AND PREVENTING ATOPIC ALLERGIC DISEASES

(71) Applicants: National Jewish Health, Denver, CO (US); Samsung Life Public Welfare Foundation, Seoul (KR)

(72) Inventors: Donald Y. M. Leung, Denver, CO (US); Byung Eui Kim, Greenwood Village, CO (US); Jihyun Kim, Seoul (KR); Kangmo Ahn, Seoul (KR)

(73) Assignees: National Jewish Health, Denver, CO (US); Samsung Life Public Welfare Foundation, Seoul (KR)

( * ) Notice: Subject to any disclaimer, the term of this patent is extended or adjusted under 35 U.S.C. 154(b) by 662 days.

(21) Appl. No.: 15/385,051

(22) Filed: Dec. 20, 2016

(65) Prior Publication Data

US 2017/0176455 A1   Jun. 22, 2017

Related U.S. Application Data

(60) Provisional application No. 62/270,793, filed on Dec. 22, 2015.

(51) Int. Cl.
*G01N 31/00* (2006.01)
*G01N 33/53* (2006.01)
*G01N 33/68* (2006.01)

(52) U.S. Cl.
CPC ..... *G01N 33/6863* (2013.01); *G01N 2333/52* (2013.01); *G01N 2800/24* (2013.01); *G01N 2800/50* (2013.01)

(58) Field of Classification Search
None
See application file for complete search history.

(56) References Cited

PUBLICATIONS

Takai: Allergology International, 2012, vol. 61, pp. 3-17.*
Fornasa et al: J Allergy Clin Immunol 2015, vol. 136, pp. 413-422.*
Masuda et al. (Clinical and Experimental Immunology, vol. 171, pp. 330-337, 2012).*
Bunyavanich et al. (Clinical and Molecular Allergy 2011, vol. 9, No. 1).*
Zhang and Zhou (Immunol Res. Jun. 2012 ; vol. 52 No. 3, pp. 211-223).*
Bunyavanich et al. (Clinical and Molecular Allergy 2011, vol. 9, No. 1) (Year: 2011).*
Zhang and Zhou (Immunol Res. Jun. 2012 ; vol. 52 No. 3, pp. 211-223) (Year: 2012).*
Ziegler (Current Opionin in Immunology, 2010, vol. 22, pp. 795-799) (Year: 2010).*
Masuda et al. (Clinical and Experimental Immunology, vol. 171, pp. 330-337, 2012) (Year: 2012).*
Broccardo et al. "Peeling off the layers: Skin taping and a novel proteomics approach to study atopic dermatitis," Journal of Allergy and Clinical Immunology, Nov. 2009, vol. 124, No. 5, pp. 1113-1115.e11.
Horimukai et al. "Application of moisturizer to neonates prevents development of atopic dermatitis," Journal of Allergy and Clinical Immunology, Oct. 2014, vol. 134, No. 4, pp. 824-830.e6.
Kelleher et al. "Skin barrier dysfunction measured by transepidermal water loss at 2 days and 2 months predates and predicts atopic dermatitis at 1 year," Journal of Allergy and Clinical Immunology, Apr. 2015, vol. 135, No. 4, pp. 930-935.e1.
Kim et al. "Thymic stromal lymphopoietin downregulates filaggrin expression by signal transducer and activator of transcription 3 (STAT3) and extracellular signal-regulated kinase (ERK) phosphorylation in keratinocytes," Journal of Allergy and Clinical Immunology, Jul. 2015, vol. 136, No. 1, pp. 205-208.e9.
Leung et al. "Deciphering the Complexities of Atopic Dermatitis: Shifting Paradigms in Treatment Approaches," Journal of Allergy and Clinical Immunology, Oct. 2014, vol. 134, No. 4, pp. 769-779.
Sano et al. "Thymic stromal lymphopoietin expression is increased in the horny layer of patients with atopic dermatitis," Clinical and Experimental Immunology, Mar. 2013, vol. 171, No. 3, 330-337.
Thyssen et al. "Causes of epidermal filaggrin reduction and their role in the pathogenesis of atopic dermatitis," Journal of Allergy and Clinical Immunology, Oct. 2014, vol. 134, No. 4, pp. 792-799.

* cited by examiner

*Primary Examiner* — Lisa V Cook
(74) *Attorney, Agent, or Firm* — Sheridan Ross P.C.

(57) ABSTRACT

The present invention is related to novel methods for identifying a population of subjects that are at risk for developing of atopic allergic diseases, and to the prevention of these allergic diseases.

12 Claims, 4 Drawing Sheets

METHODS OF DETECTING AND PREVENTING ATOPIC ALLERGIC DISEASES

CROSS-REFERENCE TO RELATED APPLICATIONS

This application claims the benefit of priority under 35 U.S.C. § 119(e) to U.S. Provisional Patent Application No. 62/270,793, filed Dec. 22, 2015. The entire disclosure of U.S. Provisional Patent Application No. 62/270,793 is incorporated herein by reference.

FIELD OF THE INVENTION

The present invention is directed toward the diagnosing and/or identification of a population of subjects that are at risk for developing an allergic disease and to the prevention and treatment of an allergic disease in such subjects.

BACKGROUND OF THE INVENTION

Per the World Allergy Organization, the natural history of atopic manifestations is referred to as "Allergic March" or "Atopic March" and is characterized by a typical sequence of immunoglobulin E (IgE) antibody responses and clinical symptoms which may appear early in life, persist over years or decades and often remit spontaneously with age. The allergic diseases that often begin early in life include atopic dermatitis (AD), food allergy, asthma and allergic rhinitis. In general, no clinical symptoms except a dry skin are detectable at birth. Although the production of IgE starts in the $11^{th}$ week of possibly gestation, no specific sensitization to food or inhalant allergens can be detected in cord blood with standard methods for measuring elevated serum IgE antibodies. The first IgE responses directed to food proteins may be observed during the first weeks or months of life. In all parts of the world they are most commonly directed to proteins from hen's egg, peanuts and cow's milk, independent of the mode of feeding (breastfeeding versus formula feeding). These strong infantile IgE antibody responses to food proteins can be considered as markers for atopic reactivity in general, since they have been demonstrated to be predictors of subsequent sensitization to other food proteins (peanuts, tree nuts) or aeroallergens from the indoor or outdoor environment. Sensitization to environmental allergens requires more time and is generally observed during the pre-school or early school-age period. In many atopic individuals, atopic dermatitis (AD) is the first clinical manifestation with the highest incidence during the first months of life, and the highest period prevalence during the first three years of life (worldallergy.org/professional/allergic_diseases_center/allergic_march/). Over 50% of patients with AD develop respiratory allergies including asthma and allergic rhinitis.

AD is a chronic inflammatory skin disorder that affects nearly 17% of children and can persist into adulthood. Advances in understanding the mechanisms underlying AD require direct sampling of AD skin. Although AD is primarily a skin disease involving infants and young children, there are no skin-based studies examining AD in this age group because of the invasiveness of skin biopsies. AD is often associated with food allergy and asthma. The abnormal skin barrier in patients with AD may allow epicutaneous absorption of environmental allergens through the skin and promote systemic allergen sensitization, which predisposes to the development of food allergy and asthma (Broccardo C J, et al. Peeling off the layers: skin taping and a novel proteomics approach to study atopic dermatitis. J Allergy Clin Immunol 2009; 124:1113-5 e1-11; Leung D Y, Guttman-Yassky E. Deciphering the complexities of atopic dermatitis: shifting paradigms in treatment approaches. J Allergy Clin Immunol 2014; 134:769-79).

AD is a complex disease with a genetic predisposition strongly influenced by innate and adaptive immune responses, as well as environmental factors, including allergen exposure, irritants', microbes, diet, stress, and air quality ((Broccardo C J, et al. Peeling off the layers: skin taping and a novel proteomics approach to study atopic dermatitis. J Allergy Clin Immunol 2009; 124:1113-5 e1-11; Leung D Y, Guttman-Yassky E. Deciphering the complexities of atopic dermatitis: shifting paradigms in treatment approaches. J Allergy Clin Immunol 2014; 134:769-79).

Because current treatment approaches are not curative, there is considerable interest in studying approaches to prevent AD as well as other infantile allergic diseases, including use of strategies to improve skin barrier or downregulate the type 2 allergic immune response. This may be due to a lack of standardization of the bacterial preparations or lack of biomarkers to identify which AD phenotype would benefit from this approach ((Broccardo C J, et al. Peeling off the layers: skin taping and a novel proteomics approach to study atopic dermatitis. J Allergy Clin Immunol 2009; 124:1113-5 e1-11; Leung D Y, Guttman-Yassky E. Deciphering the complexities of atopic dermatitis: shifting paradigms in treatment approaches. J Allergy Clin Immunol 2014; 134:769-79).

SUMMARY OF INVENTION

One embodiment of the invention relates to a method to identify a subject at risk of developing an allergic disease comprising: (a) obtaining a skin sample from the subject; (b) determining the expression level of thymic stromal lymphopoietin (TSLP) in the skin sample; and (c) comparing the expression level of TSLP in the skin sample to a control sample wherein an increased expression level of TSLP as compared to the control sample identifies the subject as being at risk to develop an allergic disease.

In another embodiment, the invention relates to a method of diagnosing and treating an allergic disease in an asymptomatic subject comprising: (a) obtaining skin sample from the subject; (b) determining the expression level of TSLP in the skin sample; (c) comparing the expression level of TSLP in the skin sample to a control sample wherein a statically significant increased expression level of TSLP as compared to the control sample identifies the subject as having an allergic disease; and (d) administering an effective amount of a topical or systemic therapeutic to the subject prior to development of allergic disease symptoms.

In any of the methods or uses described herein, the allergic disease is selected from the group consisting of atopic dermatitis, food allergy, asthma and allergic rhinitis.

In any of the methods or uses described herein, the subject is administered a moisturizer.

In any of the methods or uses described herein, the subject identified at being at risk or developing an allergic disease is administered a TSLP inhibiting agent. In any of the methods or uses described herein the TSLP inhibiting agent is selected from the group consisting of humanized antibodies that neutralize TSLP action and antibodies that bind to the TSLP receptor or its downstream effects. In one aspect, the TSLP inhibiting agent is in a pharmaceutical composition. In still another aspect, the pharmaceutical composition is administered to the subject by an administration route selected from the group consisting topical, oral, and subcutaneous.

In any of the methods or uses described herein the subject is administered an effective amount of a topical or systemic therapeutic. In one aspect, the subject is an asymptomatic subject and is administered the topical or systemic therapeutic prior to development of allergic disease symptoms. In one aspect, the topical therapeutic is selected from the group consisting of a moisturizer, topical anti-inflammatory medication and combinations thereof. In still another aspect, the method further comprises additional administration of the topical or systemic therapeutic upon development of allergic disease symptoms. In yet another aspect, the method further comprises administration of a different topical or systemic therapeutic as compared to the previously administered topical or systemic therapeutic. In still another aspect, administration of the therapeutic prevents the development of allergic disease symptoms in the subject. In yet another aspect, administration of the therapeutic delays the onset of the allergic disease or symptoms thereof. In still another aspect, administration of the therapeutic reduces the severity of the allergic disease symptoms in the subject.

Another embodiment of the invention relates to a method to determine the expression level of TSLP in a subject, comprising: (a) adhering a skin tape to the skin of the subject; (b) removing the skin tape from the skin of the subject; (c) extracting the TSLP protein and/or RNA from the removed skin tape; and (d) measuring the extracted protein and/or RNA TSLP levels.

In any of the methods or uses described herein the skin sample is obtained by a skin tape stripping method.

In any of the methods or uses described herein the skin sample is an epidermal skin sample.

In any of the methods or uses described herein the expression level of TSLP is determined by a method selected from the group consisting of mass spectrometry, Western Blotting, Elisa and PCR.

In any of the methods or uses described herein the subject is a human infant.

DETAILED DESCRIPTION OF THE INVENTION

Figure 1:
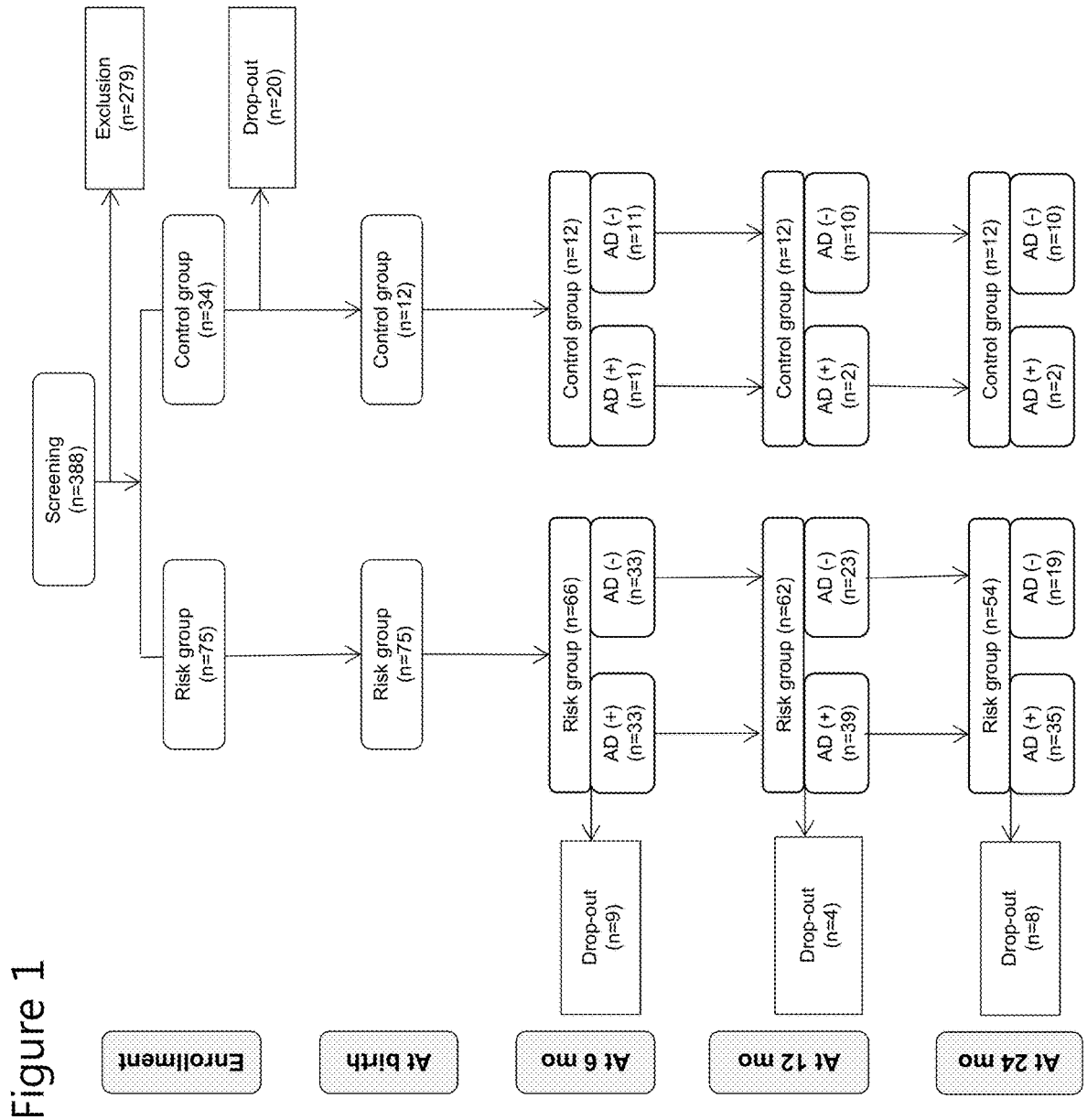
FIG. 1 shows a flow chart of the study population disclosed herein during the study period. The number of infants with AD indicates the cumulative number of patients who have developed AD at the time of evaluation.

The present invention generally relates to novel methods for predicting and/or identifying subjects predisposed to developing an allergic disease, as well as, to methods to diagnose, treat and prevent an allergic disease. These allergic diseases can include allergic diseases that often begin early in life (referred to herein as "infantile allergic diseases") and include AD, food allergies, asthma and allergic rhinitis.

The inventors have found that for primary prevention of allergic diseases such as AD, it is important to identify subjects, such as human infants, predisposed or at risk to the development of allergic diseases. The inventors have made the novel finding that increased TSLP expression in the skin, precedes the development of allergic diseases including AD, food allergies, asthma and allergic rhinitis, in infants and that skin TSLP can serve as an early biomarker for these allergic diseases.

To establish a primary prevention strategy for allergic diseases, it is important to identify biomarkers that can predict the occurrence of allergic diseases such as AD, food allergies, asthma and allergic rhinitis. The study disclosed in the Example section herein demonstrates that the expression level of skin epidermal proteins determined by a tape stripping method (also referred to as "skin tapping") can be used as biomarkers that are predictive of infantile allergic disease development.

The birth cohort study described in the Example section herein demonstrates that epidermal TSLP expression as early as 2 months of age is linked with AD development later in life. The predictive value for AD was further increased by high TSLP expression in subjects with a family history which is the strongest risk factor. It was previously determined that TSLP expressed in the horny layer of stratum corneum, like IL-4, IL-13, IL-17, IL-22, IL-25, IL-31 and IL-33, promotes Th2 type inflammation, and downregulates filaggrin expression (Sano Y, et al. Thymic stromal lymphopoietin expression is increased in the horny layer of patients with atopic dermatitis. Clin Exp Immunol 2013; 171:330-7; Kim J H, et al. Thymic stromal lymphopoietin downregulates filaggrin expression by signal transducer and activator of transcription 3 (STAT3) and extracellular signal-regulated kinase (ERK) phosphorylation in keratinocytes. J Allergy Clin Immunol 2015; 136:205-8 e9; Thyssen J P, Kezic S. Causes of epidermal filaggrin reduction and their role in the pathogenesis of atopic dermatitis. J Allergy Clin Immunol 2014; 134:792-9; Seltmann J, et al. IL-33 impacts on the skin barrier by downregulating the expression of filaggrin. J Allergy Clin Immunol 2015; 135:1659-61 e4). A recent study showed that the long isoform of TSLP exerts proinflammatory activities, whereas the short isoform plays an anti-inflammatory role (Fornasa G, et al. Dichotomy of short and long thymic stromal lymphopoietin isoforms in inflammatory disorders of the bowel and skin. J Allergy Clin Immunol 2015; 136:413-22). Stratum corneum TSLP level is reduced by moisturizer application in AD patients (Sano Y, et al. Thymic stromal lymphopoietin expression is increased in the horny layer of patients with atopic dermatitis. Clin Exp Immunol 2013; 171:330-7). This may explain how AD development is prevented by application of moisturizer to neonates (Horimukai K, Morita K, Narita M, Kondo M, Kitazawa H, Nozaki M, et al. Application of moisturizer to neonates prevents development of atopic dermatitis. J Allergy Clin Immunol 2014; 134:824-30 e6).

The term "sample" or "patient sample" or "subject sample" or "test sample" can be used generally to refer to a sample of any type which contains products that are to be evaluated by the present methods, including but not limited to, a skin sample including a skin epidermal sample, a sample of isolated cells, a tissue sample and/or a bodily fluid sample. The cells in the cell sample are not necessarily of the same type, although purification methods can be used to enrich for the type of cells that are preferably evaluated. Cells can be obtained, for example, by a tape stripping method (also referred to as "skin tapping"), scraping of a tissue, and processing of a tissue sample to release individual cells.

As used herein, the term "expression", when used in connection with detecting the expression of a gene, can refer to detecting transcription of the gene (i.e., detecting mRNA levels) and/or to detecting translation of the gene (detecting the protein produced). To detect expression of a gene refers to the act of actively determining whether a gene is expressed or not. This can include determining whether the gene expression is upregulated (or increased) as compared to a control, downregulated as compared to a control, or unchanged as compared to a control or increased or decreased as compared to a reference or control level. Therefore, the step of detecting or determining expression does not require that expression of the gene actually is upregulated or downregulated or increased or decreased, but rather, can also include detecting or determining that the expression of the gene has not changed (i.e., detecting no expression of the gene or no change in expression of the gene).

Expression of transcripts and/or proteins is measured by any of a variety of known methods in the art. For RNA expression, methods include but are not limited to: extraction of cellular mRNA and Northern blotting using labeled probes that hybridize to transcripts encoding all or part of the gene; amplification of mRNA using gene-specific primers, polymerase chain reaction (PCR), and reverse transcriptase-polymerase chain reaction (RT-PCR), quantitative PCR, and/or RNA Ampliseq, followed by quantitative detection of the product by any of a variety of means; multiplexed quantitative PCR enrichment of cDNA amplicons, followed by conversion of amplicons to sequence libraries and Next-generation based sequencing of libraries to generate digital count expression data; extraction of total RNA from the cells, which is then labeled and used to probe cDNAs or oligonucleotides encoding the gene on any of a variety of surfaces; in situ hybridization; and detection of a reporter gene.

Methods to measure protein expression levels generally include, but are not limited to: mass spectrometry, Western blot, immunoblot, enzyme-linked immunosorbant assay (ELISA), radioimmunoassay (MA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al., 1993, Anal. Biochem. 212:457; Schuster et al., 1993, Nature 365:343). Other suitable assays for measuring the binding of one protein to another include, for example, immunoassays such as enzyme linked immunoabsorbent assays (ELISA) and radioimmunoassays (RIA); or determination of binding by monitoring the change in the spectroscopic or optical properties of the proteins through fluorescence, UV absorption, circular dichroism, or nuclear magnetic resonance (NMR).

In one aspect, an increased expression level is determined when the subject's TSLP gene expression level is at least greater than one standard deviation from the mean as compared to the control and/or is determined to be significantly different (i.e., statically significantly different) and/or is higher than normal or established levels of TSLP from the control levels.

In still other aspects, the TSLP gene expression level is at least about 5%, at least about 10%, at least about 20%, at least about 30%, at least about 40%, at least about 50%, at least about 60%, at least about 70%, at least about 80%, at least about 90%, or 100% different (i.e. increased) from the expression level of the reference or control. In still another aspect, the TSLP gene expression level is at least about a 2 fold, at least about a 3 fold, at least about a 4 fold, at least about a 5 fold, at least about a 10-fold, at least about a 20 fold, at least about a 25 fold, at least about a 30 fold, at least about a 40 fold or at least about a 50 fold higher from the expression level of the reference or control. In some patient populations, TSLP will only be detectable in patients predisposed to allergic diseases and not detectable in normal non-allergic individuals.

In one aspect of the invention, the subject identified as being at risk and/or predisposed to develop allergic disease or a subject having been diagnosed as having an allergic disease, but is asymptomatic, is administered a therapeutic. In one aspect, the therapeutic is a TSLP inhibiting agent. Such TSLP inhibiting agents include but are not limited to humanized antibodies that neutralize TSLP action or bind to the TSLP receptor to prevent TSLP binding. One aspect of the invention relates to a TSLP inhibiting agent or a therapy that reduces type 2 immune responses for use in the prevention of atopic dermatitis in a subject in need thereof.

The therapeutic can be a moisturizer (also referred to as an emollient). Moistures prevent the skin from becoming dry. They can be administered, hourly, daily, twice a day, three times a day or more if the skin becomes dry. Moistures can be in the form of lotions, creams, ointments, and/or bath/shower additives. The same or different moistures can be administered to the subject at the same time or at different times. For example, a thick ointment may be used as a soap substitute as normal soap tends to dry the skin out. An ointment may be administered at bedtime followed by administration of cream during the day. An ointment may be administered on some areas of the body of the subject, while a cream may be administered to other areas of the body. The moisturizer can be administered to the subject topically.

The therapeutic can be also an anti-inflammatory drug, such as a topical steroid (including corticosteroids) or calcineurin inhibitor. These anti-inflammatory drugs can be administered to the subject as a separate treatment or can be administered in conjugation with other therapeutics. For example, a moisture can be administered to the subject first, followed by administration of the steroid.

In one aspect of the invention, the TSLP inhibiting agent, moisturizer or anti-inflammatory drug is in a pharmaceutical composition. The composition can include a pharmaceutically acceptable carrier.

In one aspect, the TSLP inhibiting agent or anti-inflammatory drug is administered to the subject by an administration route including but not limited to topical, oral, subcutaneous administration and combinations thereof.

In some aspects of the invention, the subjects can be treated by administration of one or more compounds including but not limited, corticosteroids, leukotriene antagonists, anti-cytokine antibodies, anti-cytokine receptor antibodies, anti-IgE antibody, JAK kinase inhibitors, antibiotics, a phosphodiesterase inhibitor, and combinations thereof.

In one aspect of the invention, the subject in human, and in a preferable aspect the human is an infant human. Infant as used herein is defined as up to two years (24 months) of age. In addition, an asymptomatic subject, is a subject that is not producing or showing symptoms of an allergic disease. For example, an AD asymptomatic subject is a subject that is not producing or showing symptoms of AD such as, itching; red to brownish-grey patches on the skin (especially on the hands, feet, ankles, wrists, neck, upper chest, eyelids, inside the bend of the elbows and knees, face and scalp); small, raised bumps which can leak fluid and crust over when scratched; thickened, cracked, dry, scaly skin; and raw, sensitive, swollen skin from scratching. Most often, AD begins before age 5 and may persist into adolescence and adulthood. For some AD subjects, it flares up periodically and then clears up for a time.

In one aspect, once an asymptomatic subject is diagnosed as having an allergic disease, treatment can commence immediately to reduce the severity and/or delay the onset of symptoms.

In still other aspects, the TSLP gene expression level of the subject can be determined and compared at 1 month of age, 2 months of age, 3 months of age, 4 months of age, 5 months of age, 6 month of age, 7 months of age, 8 months of age, 9 months of age, 10 months of age, 11, months of age, 12 months of age, 13 months of age, 14 months of age, 15 months of age, 16 months of age, 17 months of age, 18 months of age, 19 months of age, 20 months of age, 21 months of age, 22 months of age, 23 months of age or 24 months of age. The TSLP gene expression level of the subject can be determined at more than one age. For example, the TSLP gene expression level can be determined at 2 months of age and then again at 6 months of age.

As used herein, reference to a reference or control, means a subject who is a relevant reference or control to the subject being evaluated by the methods of the present invention. The control can be matched in one or more characteristics to the subject. In one aspect, the control can be an individual (such as an infant) with no family history of allergy and does not develop an allergic disease such as AD. No family hisotry of allergy indicates that both parents had neither allergy nor skin test reactivity to 8 common inhalant allergens (*Dermatophagoides pteronyssinus, D. farinae*, tree pollen mixture I & II, weed pollen mixture, grass pollen mixture, cat, and cockroach). The reference or control expression level used in the comparison of the methods of the present invention can be determined from one or more relevant reference or control subjects.

Another embodiment of the present invention relates to a kit for detecting the expression of TSLP. In one aspect, the kit comprises a detection agent for detecting the expression of the TSLP gene. In one aspect, the kit comprises an agent for detecting RNA expression. In still another aspect, the kit comprises an agent for detecting protein expression.

The following examples are provided for illustrative purposes, and are not intended to limit the scope of the invention as claimed herein. Any variations which occur to the skilled artisan are intended to fall within the scope of the present invention. All references cited in the present application are incorporated by reference herein to the extent that there is no inconsistency with the present disclosure.

EXAMPLE

This example demonstrates that epidermal TSLP expression as early as 2 months of age is linked with AD development later in life. The predictive value for AD was further increased by high TSLP expression in subjects with a family history which is the strongest risk factor.

Study Population

The study population (a Korean cohort) was selected according to very strict criteria. The inventors excluded parents with asthma or allergic rhinitis from the risk group unless they were sensitized to common inhalant allergens as well. Subjects with history of AD were also excluded if eczema symptoms were not found on site. Likewise, all parents with asymptomatic sensitization were excluded from the control group even though they had never presented asthma or allergic rhinitis symptoms. Finally, the inventors excluded 279 subjects out of 388 after initial screening, and successfully followed 75 infants in the risk group and 12 in the control group for 2 years.

In the prospective birth cohort study described herein, the inventors followed 75 infants in a risk group and 12 in a control group for 2 years (FIG. 1). The control group consisted of infants with both parents who had neither allergy nor skin test reactivity to 8 common inhalant allergens (*Dermatophagoides pteronyssinus, D. farinae*, tree pollen mixture I & II, weed pollen mixture, grass pollen mixture, cat, and cockroach). The risk group was defined when at least one parent had both positive skin test response and a history of asthma or allergic rhinitis, or when at least one family member had AD.

Sample Collection, Protein Extraction and Mass Spectrometry

Patients were directed to avoid showering on the day of the collection. A total of 20 consecutive D-SQUAME® tape strips (22 mm diameter, CuDerm, Dallas, Tex., USA) were performed on the volar surface of right forearm at the age of 2 months. On application of the first tape disc, 4 marks were placed around the disc with a pen so that subsequent discs could be applied to the same location. Each tape disc was placed adhesive side up in its own 6-well plate and then frozen at −80° C.

Proteins were extracted by using a buffer composed of 0.01% 3-(3-[1,1-bisalkyloxyethyl]pyridin-1-yl)propane-1-sulfonate (Protein Discovery, Knoxville, Tenn., USA) in 50 mmol/L ammonium bicarbonate with 1× HALT protease inhibitors, EDTA-free (Thermo Fisher Scientific, Rockford, Ill., USA), and 50 mmol/L dithiothreitol (Bio-Rad, Hercules, Calif., USA) and incubated on a rocker at room temperature for 1 hour. Extraction buffer was pooled from tape disc, transferred into polypropylene 1.5 mL microcentrifuge tubes, lyophilized, and stored at −80° C.

Proteins were precipitated in 300 mL ice-cold precipitation buffer consisting of 0.1% formic acid in 80:20 methanol:water (VWR, West Chester, Pa., USA; and Thermo Fisher Scientific, respectively). Samples were incubated at −20° C. and vortexed for 30 seconds every 10 minutes for 1 hour, then centrifuged at 18,000 g at 4° C. for 20 minutes. The supernatant was removed, and the protein pellet was resuspended in 8 mol/L urea (Sigma Ultra, St Louis, Mo., USA) in 100 mmol/LTRIS HC1 (pH 8.5; Thermo Fisher Scientific). Proteins were reduced with 5 mmol/L TCEP (tris[2-carboxyethyl]phosphine) (Thermo Fisher Scientific) for 20 minutes and alkylated with 500 mmol/L iodoacetamide (Bio-Rad) for 15 minutes. Urea was diluted to 2 mol/L with 100 mmol/L TRIS HCl (pH 8.5), and samples were incubated at 37° C. overnight with 100 ng trypsin (Trypsin Gold; Promega, Madison, Wis., USA). Samples were then cleaned by using PepClean C-18 spin columns (Thermo Fisher Scientific) following the manufacturer's protocol. All reagents were of the highest grade available for mass spectrometry.

Mass spectrometry was carried out as previously described by Broccardo C J, et al. (J Allergy Clin Immunol 2009; 124:1113-5 e1-11). Samples were run in triplicate on an Agilent 1200 series HPLC (Agilent Technologies, Santa Clara, Calif., USA) and Agilent ETD ion trap (model 6340) mass spectrometer with an HPLC chip to evaluate the expression of filaggrin, alpha enolase, corneodesmosin, fatty acid binding protein, serpin B3, transglutaminase 3, and thymic stromal lymphopoietin (TSLP).

Statistical Analysis

Data were analyzed using SPSS for Windows (version 23.0, SPSS, Chicago, USA). The Fisher exact test was applied to determine the differences in the proportions of gender, delivery mode, parental history of allergic diseases, parental atopy, monthly income, maternal education levels, and incidence of AD between the risk group and the control group. The Mann-Whitney U test was used to analyze the differences in birth weights, intrauterine periods, and maternal ages between the risk group and the control group.

To estimate risk factors predicting AD development by the age of 24 months, univariable and multivariable logistic regression analyses were used. In a univariable analysis, candidate variables for adjustment included epidermal protein levels, gender, parental history of allergic diseases, delivery mode, maternal education levels, move to a new house during pregnancy, mold exposure during pregnancy, exclusive breastfeeding during the first 4 months of life, and transepidermal water loss at 2 months of age. TSLP and epidermal protein levels were dichotomized according to their median values. In a multivariable regression analysis, TSLP and other variables with P value less than 0.1 in univariable analysis were selected and adjusted for each other. The combined effect of TSLP and family history was also evaluated using a multivariable logistic regression. A P value<0.05 was considered to be significant.

Results

The diagnosis of AD was based on the Hanifin and Rajka criteria, and the severity was assessed using the SCORing Atopic Dermatitis (SCORAD). Transepidermal water loss (TEWL) was measured on the volar surface of the forearm at age 2 months by a Tewameter TM300 (Courage & Khazaka, Köln, Germany). Tape stripping was done on the volar surface of the forearm at 2 months, and epidermal protein levels were measured by mass spectrometry to evaluate the expression of filaggrin, alpha enolase, corneodesmosin, fatty acid binding protein, serpin B3, transglutaminase 3 and thymic stromal lymphopoietin (TSLP) (Broccardo C J, et al. Peeling off the layers: skin taping and a novel proteomics approach to study atopic dermatitis. J Allergy Clin Immunol 2009; 124:1113-5 e1-11). Other mass spectrometry methods may also be used with similar results.

Figure 2:
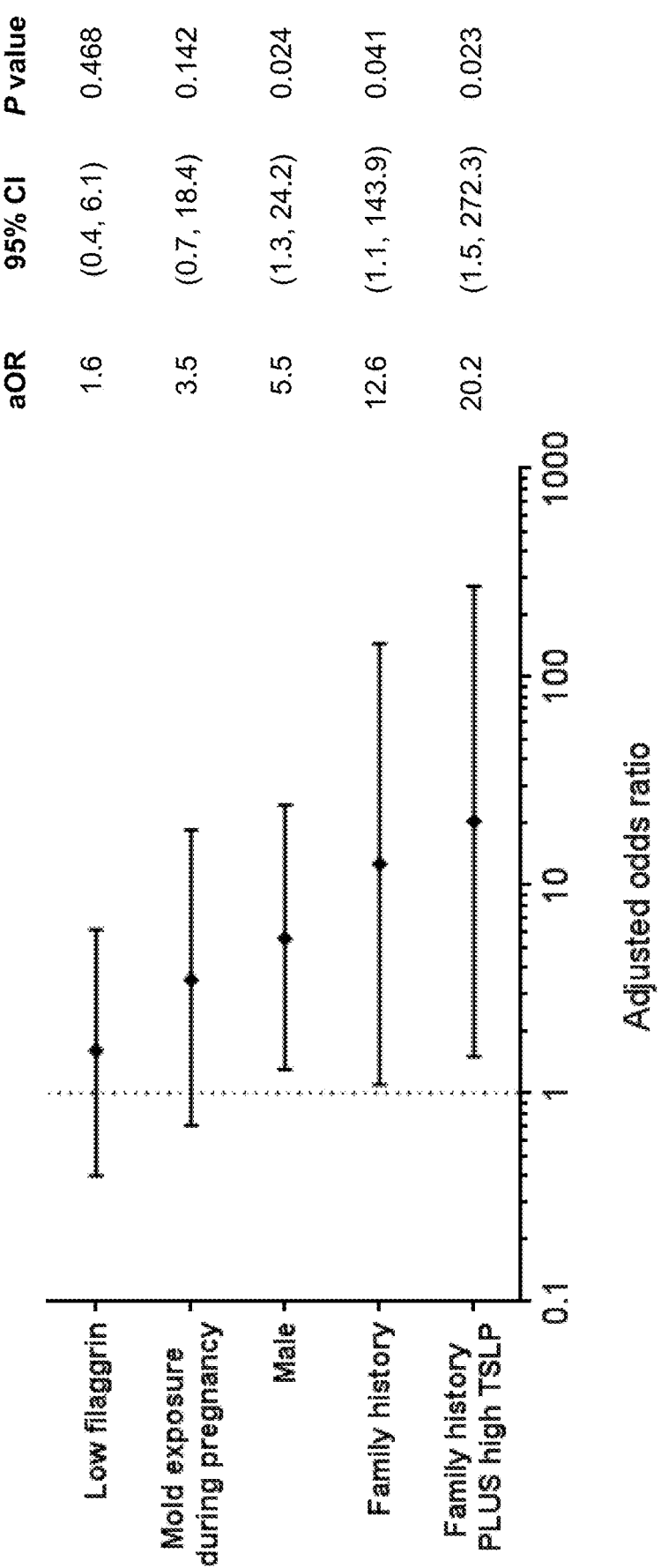
FIG. 2 shows a multivariable analysis for factors influencing AD development by 24 months of age. When thymic stromal lymphopoietin (TSLP) expression was dichotomized into low or high levels according to its median value and added to family history, the predictive value for AD development was further increased in subjects with family history and high TSLP expression than in those with family history and low TSLP expression. Male gender was also independently linked with AD development. Multivariable analysis was done after adjustment for factors with P<0.1 in univariable analysis. aOR, adjusted odds ratio; CI, confidence intervals.
Figure 3:
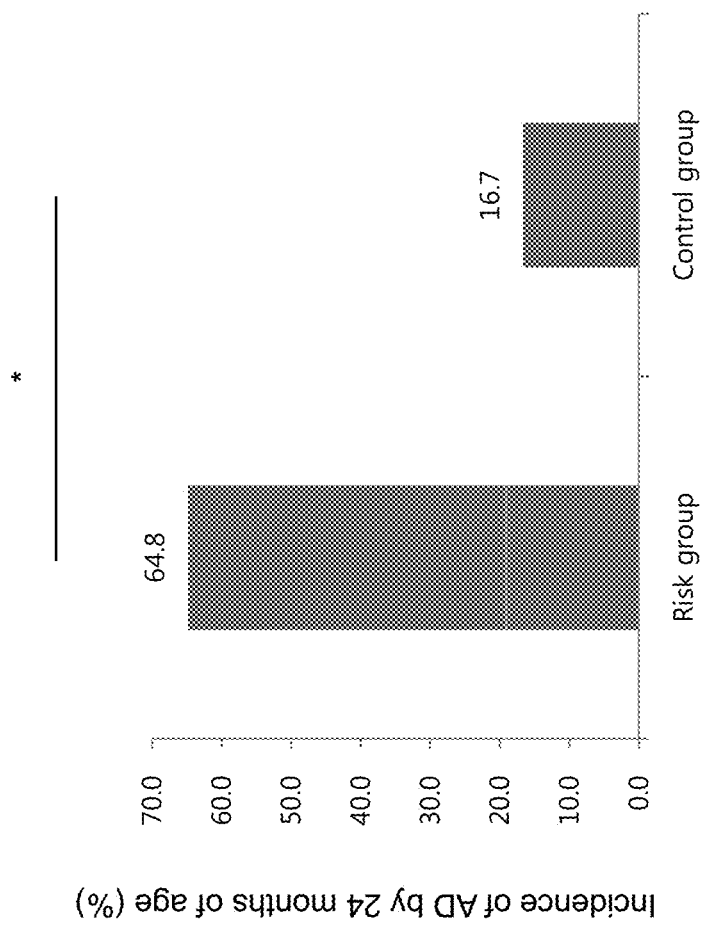
FIG. 3 shows a comparison of the incidence of AD by the age of 24 months between the risk group and the control group. Statistical analysis was done using Fisher's exact test. *P<0.05

The cumulative incidence of AD was higher in the risk group than in the control group at 24 months (64.8% vs 16.7%, P=0.003) (FIG. 2). Eczema symptoms at 12 months of age occurred mostly on the face (72.7%), but clinical AD did not appear on the forearm where tape stripping was conducted. The mean scores of SCORAD in affected infants were 13.3±5.8 and 12.9±5.4 at ages of 12 and 24 months, respectively. There was no difference between the risk group and the control group in various risk factors (Table 1).

TABLE 1

Characteristics of Study Participants:

|  | Risk group (n = 75) | Control group (n = 12) | P value |
|---|---|---|---|
| Gender (boy, %) | 43 (57.3%) | 8 (66.7%) | 0.754 |
| Birth weight (kg) | 3.2 ± 0.4 | 3.1 ± 0.5 | 0.434 |
| Intrauterine period (wk) | 39.5 ± 6.1 | 39.4 ± 6.3 | 0.696 |
| Mother's age at child's birth (yr) | 32.1 ± 2.8 | 32.8 ± 3.3 | 0.555 |
| Birth type |  |  | 0.746 |
| Vaginal delivery | 53 (70.7%) | 8 (66.7%) |  |
| Cesarean section | 22 (29.3%) | 4 (33.3%) |  |
| Paternal history of allergic diseases |  |  |  |
| Atopic dermatitis | 19 (25.3%) | 0 (0%) | 0.041 |
| Allergic rhinitis | 25 (33.3%) | 0 (0%) | 0.012 |
| Asthma | 5 (6.7%) | 0 (0%) | 0.467 |
| Maternal history of allergic diseases |  |  |  |
| Atopic dermatitis | 18 (24.0%) | 0 (0%) | <0.001 |
| Allergic rhinitis | 46 (63.0%) | 0 (0%) | <0.001 |
| Asthma | 3 (4.0%) | 0 (0%) | 0.637 |
| Paternal atopy* | 46 (63.0%) | 0 (0%) | <0.001 |
| Maternal atopy* | 50 (66.7%) | 0 (0%) | <0.001 |
| Monthly income (USD) |  |  | 0.971 |
| ≤1,799 | 9 (12.0%) | 1 (8.3%) |  |
| 1,800-3,599 | 36 (48.0%) | 6 (50.0%) |  |
| 3,600-5,399 | 22 (29.3%) | 4 (33.3%) |  |
| ≥5,400 | 8 (10.7%) | 1 (8.3%) |  |
| Maternal education |  |  | 0.546 |
| College | 4 5.3%) | 0 (0%) |  |
| High school or less | 71 (94.7%) | 12 (100.0%) |  |

*positive skin prick test to common allergens

Figure 4:
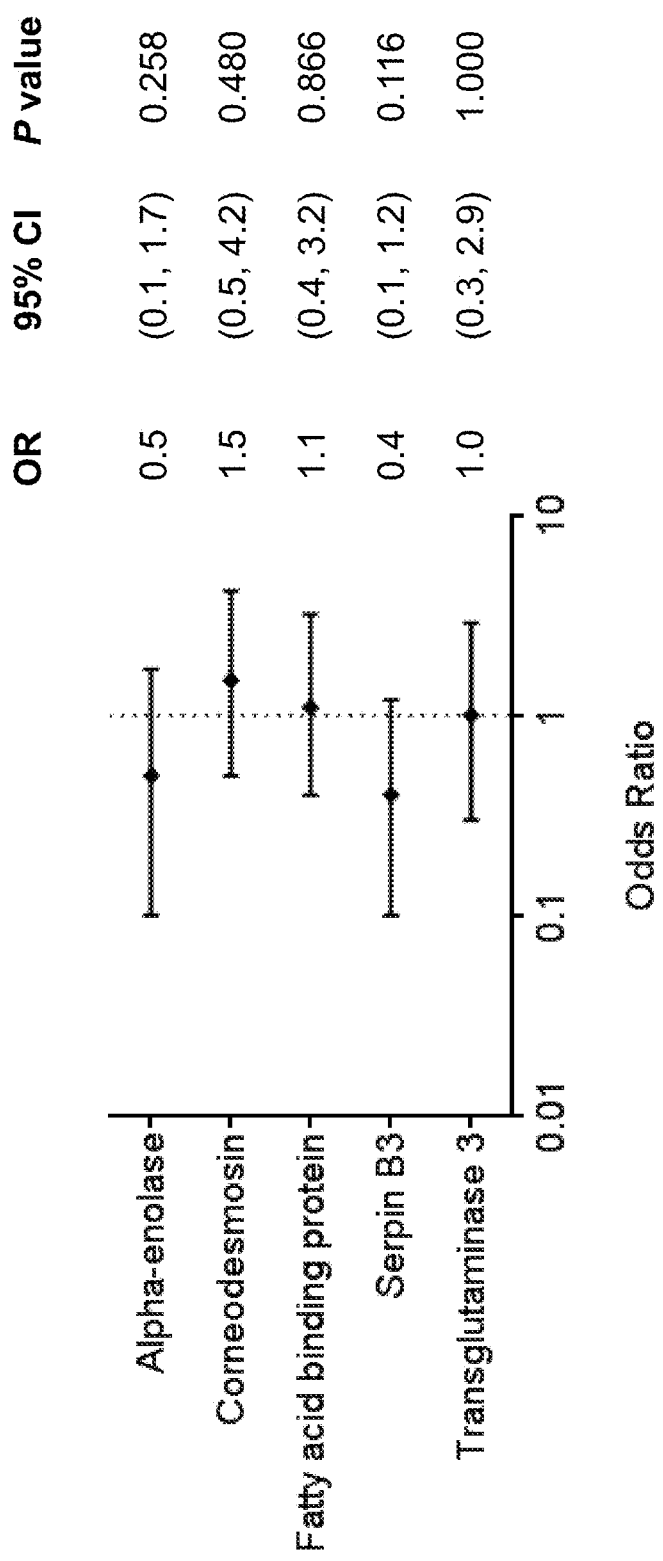
FIG. 4 shows a univariable analysis for epidermal proteins influencing AD development by 24 months of age. OR, odds ratio; CI, confidence intervals.

To estimate risk factors predicting AD development by the age of 24 months, a logistic regression model was used. A multivariable analysis was done by adjusting for TSLP and other variables with P value<0.1 in a univariable analysis (FIG. 2). When TSLP expression was dichotomized into low or high levels according to its median value, 0.83 pmol/μg skin (range 0.32-1.60 pmol/μg skin), and added to family history, adjusted odds ratio (aOR) for AD development was higher in subjects with family history and high TSLP expression (aOR=20.2, 95% Confidence Interval (CI) 1.5-272.3) than in those with family history alone (aOR=12.6, 95% CI 1.1-143.9). Male gender was also independently related with AD development (aOR=5.5, 95% CI 1.3-24.2). In contrast, other variables such as birth type, passive smoking, mold exposure during pregnancy, exclusive breastfeeding, transepidermal water loss (TEWL) on the nonlesional area of the forearm at 2 months, and filaggrin level at 2 months showed no statistical significance in a logistic regression model. The expression of alpha enolase, corneodesmosin, fatty acid binding protein, serpin B3, and transglutaminase 3 at 2 months was not predictive of AD development (FIG. 4).

In an Irish birth cohort study, increased TEWL was found before the occurrence of AD and the authors suggested that measurement of TEWL at ages of 2 days and 2 months was predictive of AD development at 1 year (Kelleher M, et al. Skin barrier dysfunction measured by transepidermal water loss at 2 days and 2 months predates and predicts atopic dermatitis at 1 year. J Allergy Clin Immunol 2015; 135: 930-5 e1). The inventors did not find an association between TEWL at 2 months and later development of AD in the study presented herein with the Korean cohort. This may be explained by the extent of inflammation in the skin. Interestingly, the mean SCORAD score in the Irish study at 6 and 12 months were 21.54±16.29 and 18.56±14.92, respectively, showing that the Irish infants had more severe AD than the Korean infants. It is plausible that subclinical skin inflammation of the Irish study population at 2 months could impair the skin barrier function as opposed to our cohort, although clinical AD was not apparent in both studies. Another possibility is that the pathobiology of AD is different in Korea versus Ireland (Noda S, et al. The Asian atopic dermatitis phenotype combines features of atopic dermatitis and psoriasis with increased Th17 polarization. J Allergy Clin Immunol 2015; 135:1254-64). Indeed, levels of Th17- and Th22-related cytokines has been found to be higher in Asian than in European American AD.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

REFERENCES

1. Broccardo C J, Mahaffey S B, Strand M, Reisdorph N A, Leung D Y. Peeling off the layers: skin taping and a novel proteomics approach to study atopic dermatitis. J Allergy Clin Immunol 2009; 124:1113-5 e1-11.
2. Sano Y, Masuda K, Tamagawa-Mineoka R, Matsunaka H, Murakami Y, Yamashita R, et al. Thymic stromal lymphopoietin expression is increased in the horny layer of patients with atopic dermatitis. Clin Exp Immunol 2013; 171:330-7.
3. Kim J H, Bae H C, Ko N Y, Lee S H, Jeong S H, Lee H, et al. Thymic stromal lymphopoietin downregulates filaggrin expression by signal transducer and activator of transcription 3 (STAT3) and extracellular signal-regulated kinase (ERK) phosphorylation in keratinocytes. J Allergy Clin Immunol 2015; 136:205-8 e9.
4. Thyssen J P, Kezic S. Causes of epidermal filaggrin reduction and their role in the pathogenesis of atopic dermatitis. J Allergy Clin Immunol 2014; 134:792-9.
5. Seltmann J, Roesner L M, von Hesler F W, Wittmann M, Werfel T. IL-33 impacts on the skin barrier by downregulating the expression of filaggrin. J Allergy Clin Immunol 2015; 135:1659-61 e4.
6. Fornasa G, Tsilingiri K, Caprioli F, Botti F, Mapelli M, Meller S, et al. Dichotomy of short and long thymic stromal lymphopoietin isoforms in inflammatory disorders of the bowel and skin. J Allergy Clin Immunol 2015; 136:413-22.
7. Horimukai K, Morita K, Narita M, Kondo M, Kitazawa H, Nozaki M, et al. Application of moisturizer to neonates prevents development of atopic dermatitis. J Allergy Clin Immunol 2014; 134:824-30 e6.
8. Leung D Y, Guttman-Yassky E. Deciphering the complexities of atopic dermatitis: shifting paradigms in treatment approaches. J Allergy Clin Immunol 2014; 134:769-79.
9. Kelleher M, Dunn-Galvin A, Hourihane J O, Murray D, Campbell L E, McLean W H, et al. Skin barrier dysfunction measured by transepidermal water loss at 2 days and 2 months predates and predicts atopic dermatitis at 1 year. J Allergy Clin Immunol 2015; 135:930-5 e1.
10. Noda S, Suarez-Fariñas M, Ungar B, Kim S J, de Guzman Strong C, Xu H, et al. The Asian atopic dermatitis phenotype combines features of atopic dermatitis and psoriasis with increased Th17 polarization. J Allergy Clin Immunol 2015; 135:1254-64.

What is claimed:
1. A method to identify and treat a subject at risk of developing atopic dermatitis comprising:
   a. obtaining a non-lesional skin sample from an asymptomatic infant subject, by a skin tape stripping method;
   b. determining an expression level of thymic stromal lymphopoietin (TSLP) in the skin sample;
   c. comparing the expression level of TSLP in the skin sample to a control sample wherein a statically significant expression level of TSLP above the expression level of TSLP in the control sample identifies the infant subject as at risk of developing atopic dermatitis; and
   d. administering a pharmaceutical composition comprising a TSLP inhibiting agent selected from the group consisting of humanized antibodies that neutralize TSLP action and antibodies that bind to the TSLP receptor and/or a moisturizer for treating atopic dermatitis.
2. The method of claim 1, wherein the expression level of TSLP is determined by a method selected from the group consisting of mass spectrometry, Western Blotting, enzyme-linked immunosorbent assay (Elisa) and polymerase chain reaction (PCR).
3. The method of claim 1, wherein the skin sample is an epidermal skin sample.
4. The method of claim 1, wherein the pharmaceutical composition is administered to the subject by an administration route selected from the group consisting topical, oral, and subcutaneous.
5. A method of diagnosing and treating atopic dermatitis in an asymptomatic infant subject, comprising:
   a. obtaining a non-lesional skin sample from an asymptomatic infant subject, by a skin tape stripping method;
   b. determining an expression level of thymic stromal lymphopoietin (TSLP) in the skin sample;
   c. comparing the expression level of TSLP in the skin sample to a control sample wherein a statically significant expression level of TSLP above the expression level of TSLP in the control sample identifies the infant subject as at risk of developing atopic dermatitis; and
   d. administering an effective amount of a topical or systemic therapeutic for treating atopic dermatitis to the subject identified as at risk of developing atopic dermatitis prior to development of atopic dermatitis symptoms.
6. The method of claim 5, wherein the expression level of TSLP is determined by a method selected from the group consisting of mass spectrometry, Western Blotting, and enzyme-linked immunosorbent assay (Elisa) and polymerase chain reaction (PCR).
7. The method of claim 5, wherein the topical therapeutic is selected from the group consisting of a moisturizer, topical anti-inflammatory medication and combinations thereof.
8. The method of claim 5, wherein the method further comprises additional administration of the topical or systemic therapeutic upon development of atopic dermatitis symptoms.
9. The method of claim 5, wherein the method further comprises administration of a different topical or systemic therapeutic as compared to the topical or systemic therapeutic administered in step d.

10. The method of claim 5, wherein the administration of the therapeutic delays the onset of the atopic dermatitis.

11. The method of claim 5, wherein administration of the therapeutic reduces the severity of the atopic dermatitis symptoms in the subject.

12. The method of claim 5, wherein the skin sample is an epidermal skin sample.

\* \* \* \* \*